(12) United States Patent
Tsuge et al.

(10) Patent No.: US 8,394,613 B2
(45) Date of Patent: Mar. 12, 2013

(54) POLYHYDROXYALKANOIC ACID COPOLYMER AND PROCESS FOR PREPARING SAME

(75) Inventors: Takeharu Tsuge, Yokohama (JP); Tetsuya Yamamoto, Yokohama (JP); Asahi Kitagawa, Yokohama (JP)

(73) Assignee: Tokyo Institute of Technology, Tokyo (JP)

(*) Notice: Subject to any disclaimer, the term of this patent is extended or adjusted under 35 U.S.C. 154(b) by 163 days.

(21) Appl. No.: 12/996,308

(22) PCT Filed: Apr. 22, 2009

(86) PCT No.: PCT/JP2009/058429
§ 371 (c)(1),
(2), (4) Date: Dec. 3, 2010

(87) PCT Pub. No.: WO2009/147918
PCT Pub. Date: Dec. 10, 2009

(65) Prior Publication Data
US 2011/0081692 A1 Apr. 7, 2011

(30) Foreign Application Priority Data
Jun. 5, 2008 (JP) .................................. 2008-148076

(51) Int. Cl.
*C12P 7/62* (2006.01)
(52) U.S. Cl. ........................................................ 435/135
(58) Field of Classification Search .................. None
See application file for complete search history.

(56) References Cited

U.S. PATENT DOCUMENTS
6,569,990 B1   5/2003 Noda

FOREIGN PATENT DOCUMENTS

| CN | 1301310 A | 6/2001 |
|---|---|---|
| CN | 101184843 A | 5/2008 |
| EP | 0304293 A2 | 8/1988 |
| JP | 64-069622 A | 3/1989 |
| JP | 01156320 A | 6/1989 |
| JP | 05-015383 A | 1/1993 |
| JP | 2008094886 A | 4/2008 |

OTHER PUBLICATIONS

ISR for PCT/JP2009/058429 mailed Aug. 18, 2009.

*Primary Examiner* — Tekchand Saidha
*Assistant Examiner* — Md. Younus Meah
(74) *Attorney, Agent, or Firm* — Lowe Hauptman Ham & Berner, LLP (57) ABSTRACT

A PHA copolymer comprising (R)-3-hydroxy-4-methyl valeric acid units and a production method thereof are provided.
A polyhydroxyalkanoic acid copolymer comprising at least (R)-3-hydroxy-4-methyl valeric acid units; and a method of producing a polyhydroxyalkanoic acid copolymer comprising at least (R)-3-hydroxy-4-methyl valeric acid units, wherein in the presence of a carbon source and a precursor of (R)-3-hydroxy-4-methyl valeric acid, a transformant in which the gene of polyhydroxyalkanoic acid-polymerizing enzyme has been introduced in a microorganism selected from *Escherichia coli*, *Ralstoniau* sp., and *Pseudomonas* sp. is cultured, and from the culture obtained a polyhydroxyalkanoic acid copolymer comprising at least (R)-3-hydroxy-4-methyl valeric acid units is collected.

12 Claims, 7 Drawing Sheets

POLYHYDROXYALKANOIC ACID COPOLYMER AND PROCESS FOR PREPARING SAME

RELATED APPLICATIONS

The present application is national phase of International Application Number PCT/JP2009/058429 filed Apr. 22, 2009, and claims priority from, Japanese Application Number 2008-148076 filed Jun. 5, 2008.

FIELD OF THE INVENTION

The present invention relates to a polyhydroxyalkanoic acid copolymer, and a method of preparing it. Specifically, the present invention relates to a polyhydroxyalkanoic acid copolymer containing at least (R)-3-hydroxy-4-methyl valeric acid units, and a method of preparing it.

BACKGROUND OF THE INVENTION

Polyhydroxyalkanoic acid (PHA) is a polyester which microorganisms accumulate in the cell. In recent years, PHA is attracting attention not only as a biodegradable plastic material but also as a plastic material derived from biomass. The most common PHA is a homopolymer (hereinafter referred to as "P(3HB)") having (R)-3-hydroxybutanoic acid (3HB) as the building block. However, P(3HB) has drawbacks that it is highly crystallizable and lacks flexibility. Thereafter, a method of producing a PHA copolymer (hereinafter referred to as "P(3HB-co-3HHx)") consisting of 3HB and (R)-3-hydroxyvaleric acid (3HV) using *Ralstonia eutropha* having a high PHA-accumulating potential, was developed (Kokai (Japanese Unexamined Patent Publication) No. 57-150393, or Kokai (Japanese Unexamined Patent Publication) No. 59-220192). There was little enhancement in flexibility, since 3HB and 3HV cocrystallize.

In recent years, a method of producing a copolymer (hereinafter referred to as "P(3HB-co-3HHx)") consisting of 3HB and (R)-3-hydroxyhexanoic acid (3HHx) was developed, which enabled the production of a highly flexible polyhydroxyalkanoic acid (Kokai (Japanese Unexamined Patent Publication) No. 5-93049, or Kokai (Japanese Unexamined Patent Publication) No. 7-265065). In the methods described in these publications, P(3HB-co-3HHx) is produced from a plant oil by means of a soil bacterium *Aeromonas caviae*.

The inventors of the present invention reported that a copolymer (hereinafter referred to as "P(3HB-co-3HA)" wherein 3HA is a $C_4$-$C_{12}$ (R)-3-hydroxyalkanoic acid) consisting of 3HB and (R)-3-hydroxyalkanoic acid (3HA) can be produced from a plant oil by means of a recombinant in which a mutant of PHA synthetase gene derived from *Pseudomonas* sp. was inserted into a deletion mutant (PHB$^-$4 strain) of PHA synthetase gene derived from *Ralstonia eutropha* (Kokai (Japanese Unexamined Patent Publication) No. 2007-125004).

On the other hand, homopolymers and copolymers thereof comprising as the building blocks 3-hydroxyalkanoic acid having branched alkyl groups have been reported (Int. J. Biol. Macromol., 1990, Vol. 12, pp. 92-101). However, generally, in the production of polymers comprising as the building blocks 3-hydroxyalkanoic acid having branched alkyl groups, difficulty in controlling monomer composition makes difficult the synthesis of a polymer in terms of the physical properties of the material, and in said publication as well, the branched alkyls are limited to branched octanoic acid and the physical properties were not disclosed.

SUMMARY OF THE INVENTION

Thus, in order to produce a novel polyhydroxyalkanoic acid having a further higher flexibility, it is an object of the present invention to provide a copolymer of polyhydroxyalkanoic acid comprising at least (R)-3-hydroxy-4-methyl valeric acid (hereinafter sometimes referred to as "3H4MV") units, and a method for producing it. As used herein, "(R)-3-hydroxy-4-methyl valeric acid" is synonymous with "(R)-3-hydroxyisohexanoic acid."

As a result of an intensive and extensive research considering the above circumstances, the inventors of the present invention have found that a novel polyhydroxyalkanoic acid copolymer comprising (R)-3-hydroxy-4-methyl valeric acid units can be obtained in a conventional system for synthesizing polyhydroxyalkanoic acid by culturing a host microorganism having the gene of polyhydroxyalkanoic acid-polymerizing enzyme introduced therein in the presence of a carbon source, and that by adding a precursor of (R)-3-hydroxy-4-methyl valeric acid at the time of culturing, a polyhydroxyalkanoic acid copolymer (hereinafter simply referred to as "PHA copolymer" or "PHA") having a high composition ratio of (R)-3-hydroxy-4-methyl valeric acid units can be efficiently produced, and therefore have completed the present invention.

Thus, (1) the present invention provides a polyhydroxyalkanoic acid copolymer comprising at least (R)-3-hydroxy-4-methyl valeric acid units.

(2) The present invention provides the polyhydroxyalkanoic acid copolymer according to (1) comprising (R)-3-hydroxy-4-methyl valeric acid units and (R)-3-hydroxybutanoic acid units.

(3) The present invention provides the polyhydroxyalkanoic acid copolymer according to (2) comprising (R)-3-hydroxy-4-methyl valeric acid units, (R)-3-hydroxybutanoic acid units, (R)-3-hydroxyvaleric acid units, and optionally (R)-3-hydroxyhexanoic acid units.

(4) The present invention provides the polyhydroxyalkanoic acid copolymer according to (1) comprising 14 mol % or more of (R)-3-hydroxy-4-methyl valeric acid units.

(5) The present invention provides the polyhydroxyalkanoic acid copolymer according to (1) comprising 14 mol %-40 mol % of (R)-3-hydroxy-4-methyl valeric acid units.

(6) The present invention provides a method of producing a polyhydroxyalkanoic acid copolymer, wherein in the presence of a carbon source and a precursor of (R)-3-hydroxy-4-methyl valeric acid, a transformant in which the gene of polyhydroxyalkanoic acid-polymerizing enzyme has been introduced in a microorganism selected from *Escherichia coli*, *Ralstonia* sp., and *Pseudomonas* sp., is cultured, and from the culture obtained a polyhydroxyalkanoic acid copolymer comprising at least (R)-3-hydroxy-4-methyl valeric acid units is collected.

(7) The present invention provides the production method according to (6), wherein said precursor is selected from 4-methyl valeric acid, 4-methyl pentene acid, and a mixture thereof.

(8) The present invention provides the production method according to (6) or (7), wherein said precursor is added at a concentration of 0.1-5.0 g/L.

(9) The present invention provides the production method according to any one of (6) to (8), wherein said gene of polyhydroxyalkanoic acid-polymerizing enzyme is derived from a microorganism selected from *Pseudomonas* sp. strain 61-3, *Pseudomonas stutzeri*, A33, *Allochromatium vinosum*, *Bacillus megaterium*, *Bacillus cereus*, *Bacillus* sp. INT005, *Lamprocystis roseopersicina*, *Norcardia corallina*, *Rhodobactor shaeroides*, *Ralstonnia eutropha*, *Rhodococcus* sp. NCIMB 40126, *Thiocapsa pfennigii*, *Aeromonas caviae*, and *Aeromonas hydrophila*.

(10) The present invention provides the production method according to (9), wherein said gene of polyhydroxyalkanoic acid-polymerizing enzyme is derived from *Pseudomonas* sp. strain 61-3 (DDBJ Accession No. AB014758) or *Aeromonas caviae* (GenBank Accession No. D88825).

(11) The present invention provides the production method according to (10), wherein said gene of polyhydroxyalkanoic acid-polymerizing enzyme encodes a mutant of polyhydroxyalkanoic acid-polymerizing enzyme, in which asparagine at position 149 of polyhydroxyalkanoic acid-polymerizing enzyme derived from *Aeromonas caviae* (GenBank Accession No. D88825) has been replaced with serine and aspartic acid at position 171 has been replaced with glycine.

(12) The present invention provides the method according to any one of (6) to (11), wherein said carbon source is a monosaccharide.

(13) The present invention provides the method according to any one of (12), wherein said carbon source is fructose.

(14) The present invention provides the method according to any one of (1) to (5), wherein said carbon source is a shaped body comprising a polyhydroxyalkanoic acid copolymer.

(15) The present invention provides a shaped body according to (14) which is a film.

In accordance with the production method of the present invention, a PHA copolymer comprising at least (R)-3-hydroxy-4-methyl valeric acid units can be produced in inexpensive and efficient manners. Said PHA copolymer is sufficiently strong and flexible, easy to process to films etc., and thus an industrially useful polymer material.

BEST MODE FOR CARRYING OUT THE INVENTION

Figure 1:
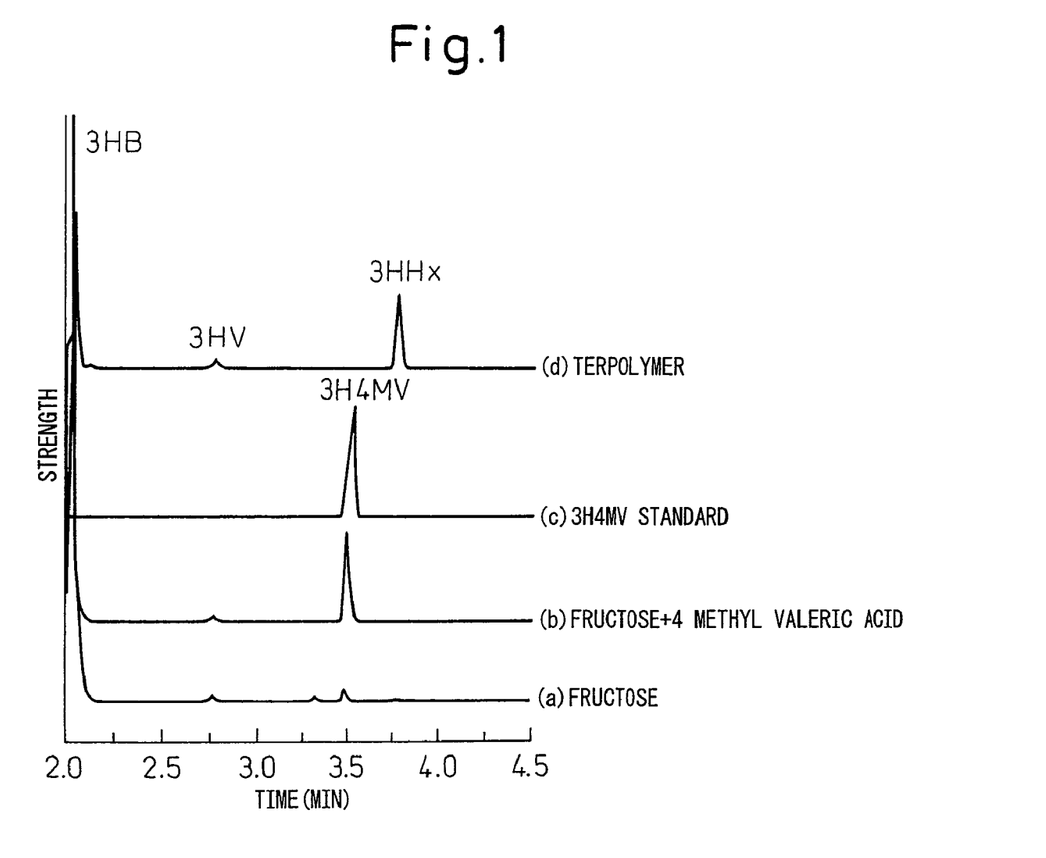
FIG. 1 is a drawing that shows the GC-MS analysis of a PHA copolymer synthesized by *Ralstonia eutropha* and the chemically-synthesized 3H4MV. (a) A m/z 103 ion chromatogram of PHA synthesized from fructose; (b) A m/z 103 ion chromatogram of PHA synthesized from fructose and 4-methyl valeric acid (4MV); (c) A m/z 103 ion chromatogram of a chemically synthesized 3H4MV (3H4MV standard); (d) A m/z 103 ion chromatogram of a terpolymer P(3HB-co-3HV-co-3HHx). The temperature program of GC started with 100° C. for one minute, followed by temperature rise to 280° C. in successive steps of 8° C./minute.

It was found for the first time by the present inventors that the PHA copolymer of the present invention comprising (R)-3-hydroxy-4-methyl valeric acid (3H4MV) units can be obtained in a conventional system for synthesizing polyhydroxyalkanoic acid by culturing a host microorganism having the gene of polyhydroxyalkanoic acid-polymerizing enzyme introduced therein in the presence of a carbon source, although the composition ratio of (R)-3-hydroxy-4-methyl valeric acid units is low (see FIG. 1). It was also demonstrated that by adding a precursor of 3H4MV at the time of culturing, a copolymer having an increased composition ratio of 3H4MV units can be produced.

Specifically, the PHA copolymer of the present invention comprises at least 3H4MV units represented by the following formula (I):

The content of 3H4MV units in the PHA copolymer of formula (I) may be preferably 14 mol % or more, and more preferably 14 mol % to 40 mol %. When the content of 3H4MV units is less than 14 mol %, the PHA copolymer may easily crystallize and the PHA copolymer obtained may be brittle. On the other hand, when the content of the 3H4MV units exceeds 40 mol %, the copolymer may be elastomeric.

The PHA copolymer of the present invention is preferably a copolymer P(3HB-co-3H4MV) that is represented by the following formula (II):

wherein x and y represent the numbers of repeats, and each independently being an integer of 1-20,000, and that comprises (R)-3-hydroxybutanoic acid (3HB) units and 3H4MV units.

Also, the PHA copolymer of the present invention may be preferably a copolymer P(3HB-co-3HV-co-3H4MV) that further comprises (R)-3-hydroxyvaleric acid (3HV) in addition to the 3HB units and 3H4MV units, and represented by the following formula (III):

(III)

wherein x, y and z represent the numbers of repeats, and each independently being an integer of 1-20,000. For the copolymer P(3HB-co-3HV-co-3H4MV), the content of 3HV in said copolymer may be preferably as low as possible in order for the copolymer to have a high flexibility, as, for example, the content of 1.6 mol % or less does not harm the flexibility. Optionally, the copolymer P(3HB-co-3HV-co-3H4MV) may further comprise (R)-3-hydroxyhexanoic acid units.

The polyhydroxyalkanoic acid copolymer of the present invention may be produced by culturing a transformant in which the gene of polyhydroxyalkanoic acid-polymerizing enzyme has been introduced in a host in the presence of a carbon source and a precursor of 3H4MV, and collecting a polyhydroxyalkanoic acid copolymer comprising (R)-3-hydroxy-4-methyl valeric acid units from the culture obtained.

A transformant in which the gene of polyhydroxyalkanoic acid-polymerizing enzyme has been introduced may be obtained by introducing, into the host cell, a plasmid that may be obtained by inserting the gene of polyhydroxyalkanoic acid-polymerizing enzyme and the gene of a known monomer-supplying enzyme into a broad-host-range vector for expressing the gene of interest in the host.

As broad-host-range vectors for expressing the gene of interest in the host, there can be mentioned vectors having the mob region having a migration ability such as pBBR1MCS-2, pJRD215 and pLA2917.

As the gene of polyhydroxyalkanoic acid-polymerizing enzyme, there can be mentioned those derived from microorganisms selected from *Pseudomonas* sp. strain 61-3, *Pseudomonas stutzeri*, *Pseudomonas* sp. A33, *Allochromatium vinosum*, *Bacillus megaterium*, *Bacillus cereus*, *Bacillus* sp. INT005, *Lamprocystis roseopersicina*, *Norcardia corallina*, *Rhodobactor shaeroides*, *Ralstonnia eutropha*, *Rhodococcus* sp. NCIMB 40126, *Thiocapsa pfennigii*, *Aeromonas caviae*, and *Aeromonas hydrophila*. Among them, the polyhydroxyalkanoic acid-polymerizing enzyme derived from *Pseudomonas* sp. strain 61-3 has an ability of accumulating the copolymer P(3HB-co-3HHx) (3HA: $C_4$-$C_{12}$ (R)-hydroxyalkanoic acid) in the cell, and the polyhydroxyalkanoic acid-polymerizing enzyme derived from *Aeromonas caviae* has an ability of accumulating the copolymer P(3HB-co-3HA) (3HA: $C_3$-$C_7$ (R)-hydroxyalkanoic acid), and thus are particularly preferred.

Also, the gene of polyhydroxyalkanoic acid-polymerizing enzyme may be a gene that encodes a mutant of the above polyhydroxyalkanoic acid-polymerizing enzyme. Such a gene encodes a protein that consists of an amino acid sequence wherein one or a few amino acids have been deleted, substituted or added in the amino acid sequence of the wild type polyhydroxyalkanoic acid-polymerizing enzyme, and that has a polyhydroxyalkanoic acid-polymerizing activity. As such a mutant, there can be specifically mentioned a mutant (NSDG mutant) in which asparagine at position 149 of the polyhydroxyalkanoic acid-polymerizing enzyme derived from *Aeromonas caviae* has been replaced with serine and aspartic acid at position 171 with glycine. A method of producing said NSDG mutant is described in detail in FEMS Microbial Lett, 277 (2007), pp. 217-222.

As the known monomer-supplying gene, there can be mentioned phbA, phbB, phaB and phbB derived from *Ralstonia eutropha* (Peoples, O. P. and Sinskey, A. J., J. Biol. Chem. 264: 15293-15297 (1989)), phaJ derived from *Aeromonas caviae*, (Fukui, T. and Doi, Y., J. Bacteriol. 179: 4821-4830 (1997)), and the like.

As the vector for microbial expression into which the gene of polyhydroxyalkanoic acid-polymerizing enzyme and the monomer-supplying gene are inserted, a known vector having a promoter, a ribosome binding site, a gene cloning site, a terminator, etc., may be used.

As the host, for example, microbial cells of *Escherichia coli*, *Ralstonia* sp., and *Pseudomonas* sp., etc., may be mentioned, because they have excellent growth properties when saccharides and lipids are used as the carbon source, their microbial strains are highly safe, and the separation of the cells and the culture liquid is relatively easy. In accordance with the present invention, *Ralstonia eutropha* strain PHB⁻4 which is deficient in PHA-accumulation potential of *Ralstonia eutropha* strain PHB⁻4 may specifically used.

At present, no efficient method of transforming the gene of polyhydroxyalkanoic acid-polymerizing enzyme ($phaCl_{Ps}$) derived from *Pseudomonas* sp. strain 61-3 into *Ralstonia eutropha* strain PHB⁻4 has been established, but the $phaCl_{Ps}$ gene can be reproducibly transmitted through conjugation. Specifically, to a broad-host-range vector for expressing the gene of interest in *Ralstonia eutropha*, a DNA fragment of the above plasmid comprising the $phaCl_{Ps}$ gene and a known monomer-supplying gene may be ligated. The plasmid obtained by the ligation may be transformed in *E. coli* in which the tra region directly involved in DNA transfer has been integrated into the chromosome, and then the plasmid obtained may be contacted with *Ralstonia eutropha* strain PHB⁻4. The transformation of *E. coli* may be conducted by, for example, the calcium method (Lederberg. E. M. et al., J. Bacteriol. 119, 1072 (1974)), the electroporation method (Current Protocols in Molecular Biology, Vol. 1, pp. 184, 1994), etc.

As the precursor of 3H4MV, for example, 4-methylvaleric acid, 4-methylpentene acid, or a mixture thereof may preferably be used. The amount of the precursor of 3H4MV added may be preferably in the range of about 0.1 to about 5.0 g/L, and more preferably in the range of about 0.5 to about 2.0 g/L.

As the carbon source, a saccharide, a lipid etc., for example, may be used. As the saccharide, there can be mentioned, for example, glucose, fructose, galactose, xylose, arabinose, saccharose, maltose, starch, starch-hydrolyzates, and the like. As the lipid, a plant oil may be preferred, and there can be mentioned, for example, soy bean oil, corn oil, cotton seed oil, coconut oil, palm oil, palm kernel oil, or fractions thereof such as palm W olein oil (a low-boiling fraction obtained by conducting the solvent-free fractionation of palm oil twice), palm kernel oil olein (a low-boiling fraction obtained by conducting the solvent-free fractionation of palm once), or a synthetic oil obtained by chemically or biochemically treating these oils or their fractions, or a mixed oil thereof.

The culturing temperature is temperature at which microorganisms can grow, and may be preferably 15-40° C., more preferably 20-40° C., and most preferably 28-34° C. The culturing time may not be specifically limited, but for the batch culture, 1-7 days is preferred, and continuous culture may also be used. The culture medium may not be specifically limited as long as the host of the present invention can utilize it. A culture medium containing nitrogen sources, mineral salts, other organic nutrients etc., in addition to carbon sources, may be used.

As the nitrogen source, there can be mentioned, for example, ammonia, an ammonium salt such as ammonium chloride, ammonium sulfate, diammonium hydrogen phosphate, peptone, meat extract, yeast extract, and the like.

As mineral salts, there can be mentioned, for example, monopotassium phosphate, dipotassium phosphate, magnesium hydrogen phosphate, magnesium sulfate, sodium chloride, and the like.

As other nutrients, there can be mentioned, for example, amino acids such as glycine, alanine, serine, threonine and proline; vitamins such as vitamin B1, vitamin B12, biotin, nicotinamide, pantothenic acid and vitamin C.

The recovery of the PHA copolymer of the present invention from the cells may be carried out by, for example, the following method. After the culturing is completed, the cells are separated from the culture liquid using a centrifuge etc. After the cells are washed in distilled water, methanol, etc., dried, and the copolymer is extracted with an organic solvent such as chloroform. Subsequently, from the organic solvent solution containing this copolymer, the cells are removed by filtration, etc., and a poor solvent such as methanol and hexane is added to the filtrate to precipitate the copolymer. From the copolymer that precipitated, the supernatant is removed by filtration or centrifugation, and dried to recover the copolymer. The copolymer obtained may be analyzed by, for example, gas chromatography or nuclear magnetic resonance.

The PHA copolymer of the present invention may be processed into a shaped body such as a film and a sheet. The thickness of the film is not specifically limited and may be generally 1 mm or less, preferably 0.5 mm or less.

The film of the present invention may be obtained by solution-casting, injection molding, press molding, blow molding etc., with solution-casting being preferred in order to obtain a colorless transparent film in a simple manner. Also, for the purpose of enhancing mechanical properties, the film of the present invention may be subjected to heat treatment at a high temperature. The temperature for heat treatment may vary depending on the type of the copolymer, but it may be usually performed at the range of 50-200° C. Furthermore, by stretching process, the mechanical properties such as tensile strength and modulus of elasticity of the film of the present invention may be further enhanced.

Furthermore, within the scope that does not ruin the purpose of the present invention, various additives generally used for films, such as a UV absorber, a thermal stabilizer, an antioxidant and a colorant, may be added to the shaped body of the present invention.

The PHA copolymer of the present invention comprising (R)-3-hydroxy-4-methyl valeric acid units has sufficient strength and flexibility, and thus is useful for use in medical materials, packaging materials for foods etc. agricultural vinyl sheets and waste bags.

EXAMPLES

The present invention will now be explained in detail with reference to examples, but it should be noted that the present invention is not limited to them in any way.

Materials and Preparation Methods
(1) Microorganisms
  (a) *Escherichia coli* Strain S17-1 (Obtained from H. G. Schlegel (Georg-August-Universitat, Germany))
  (b) *Ralstonia eutropha* PHB$^-$4 (DSM541, a PHA-Accumulation Potential-Deficient Strain of *Ralstonia eutropha* H16, Obtained from DSM of Germany)
(2) Medium
  (a) Luria-Bertani (LB) Medium
  Ten g of Bacto trypton, 5 g of yeast extract and 10 g of NaCl were dissolved in 1 L of deionized water, and autoclaved at 121° C. for 20 minutes, to prepare a liquid medium. The agar medium was prepared by adding agar to the above components to 1.5-2% (wt/vol) followed by autoclaving. An antibiotic (kanamycin: the final concentration 50 μg/mL) was added to both the liquid medium and the agar medium after autoclaving.
  (b) Nutrient-Rich (NR) Medium (pH 7.0)
  Ten g of Bacto trypton, 2 g of yeast extract and 10 g of meat extract were dissolved in 1 L of deionized water, autoclaved at 121° C. for 20 minutes, and then an antibiotic (kanamycin: the final concentration 50 μg/mL) was added.
  (c) Simmons Citrate Medium
  Two g of sodium citrate dihydrate, 5 g of NaCl, 1 g of $NH_4H_2PO_4$, 1 g of $K_2HPO_4$ and a 0.2 g/mL $MgSO_4$ solution were dissolved in 1 L of deionized water, and autoclaved at 121° C. for 20 minutes to prepare a liquid medium. The agar medium was prepared by first adjusting pH of the liquid medium to 6.9, and then, in order to prevent browning, the liquid medium and the agar component were separately autoclaved at 121° C. for 20 minutes, and then they were then mixed. Furthermore, a solution of $MgSO_4 \cdot 7H_2O$ prepared at 200 g/L was filter-sterilized, and a 1/1000 amount thereof relative to the total medium and an antibiotic (kanamycin: the final concentration 50 μg/mL) were added.
  (d) MS Medium
  Mineral medium (pH 7.0): 1.5 g of $K_2HPO_4$, 9.0 g of $Na_2HPO_4 \cdot 12H_2O$, 0.5 g of $NH_4Cl$ and 0.5 g of NaCl were dissolved in 1 L of deionized water, autoclaved at 121° C. for 20 minutes, and then 0.2 g of $MgSO_4 \cdot 7H_2O$ and 1 ml of a trace metal salt medium and 50 mg of kanamycin were added to prepare the medium.
  The trace metal salt medium (0.1 N HCl) was prepared by dissolving 0.218 g of $CoCl_2 \cdot 6H_2O$, 9.7 g of $FeCl_3$, 7.8 g of $CaCl_2$, 0.118 g of $NiCl_3 \cdot 6H_2O$, 0.105 g of $CrCl_3 \cdot 6H_2O$ and 0.156 g of $CuSO_4 \cdot 5H_2O$ into 1 L of deionized water.
(3) Plasmid
  (a) pBBR"1Cl$_{Ps}$AB$_{Re}$
  To a pGEM-T vector (obtained from Promega), the PHA synthetase gene phaCl$_{Ps}$ (DDBJ Accession No. AB014758) derived from *Pseudomonas* sp. strain 61-3 and a monomer-supplying gene phaAB$_{Re}$ (GenBank Accession No. J04987) derived from *Ralstonia eutropha* were inserted to prepare pGEM"Cl$_{Ps}$AB$_{Re}$.
  The pGEM"Cl$_{Ps}$AB$_{Re}$ plasmid was transformed into *E. coli* strain DH5α, and cultured in an antibiotic-containing LB agar medium at 37° C. for 12 hours. A single colony formed on the plate was picked up, inoculated to 1.7 mL of the antibiotic-containing LB medium, and cultured under shaking at 160/min at 37° C. for 12 hours. From the culture liquid, *E. coli* strain DH5α was recovered, and using 75 μl of the TE solution (10 mM Tris-HCl, 1 mM EDTA, pH 8.0), plasmid was extracted with the Rapid Plasmid Miniprep System (manufactured by MARLIGEN BIOSCIENCE).
  The plasmid extracted as above was digested with BamHI, and was subjected to electrophoresis using a 0.8% agarose gel (manufactured by TaKaRa). Then, the gel of the separated DNA fragment of interest was excised, and purified using the Rapid Gel Extraction System (manufactured by MARLIGEN BIOSCIENCE). At this time, 50 µl of the TE solution was used for elution. Furthermore, the obtained DNA fragment was concentrated by ethanol precipitation, and dissolved in 10 µl of the TE solution.

Four µl of the inserted DNA fragment thus obtained was mixed with 1 µl of pBBR1MCS-2 vector (obtained from M. E. K. Kovach, Louisiana State University, USA), to which 5 µl of DNA Ligation kit ver. 2 (manufactured by TaKaRa) was added, and then allowed to react at 16° C. for about 2-3 hours to construct a plasmid pBBR1"$Cl_{Ps}AB_{Re}$ that has a BamHI fragment (containing pha$Cl_{Ps}$ and pha$AB_{Re}$) of pGEM"$Cl_{Ps}AB_{Re}$ inserted therein.

(b) pBBREE32d13

A plasmid pBBREE32d13 was constructed in a manner similar to the above (a), except that the gene (pha$Cl_{Ps}$) of polyhydroxyalkanoic acid-polymerizing enzyme derived from *Pseudomonas* sp. strain 61-3 was replaced with the PHA synthetase gene (pha$C_{AC}$) (GenBank Accession No. D88825).

(4) Analytical Method of the Structure and Physical Properties of PHA Copolymer (a) Gas Chromatography (GC)

The content of PHA copolymer in the cell and its composition were determined using gas chromatography (Braunegg et al., 1978). First, 10-15 mg of the dry cells obtained was weighed into a pressure-resistant glass tube, to which 2 mL of a sulfuric acid-methanol solution (sulfuric acid: methanol=15 vol %:85 vol %) and 2 mL of chloroform were added, the tube was closed tightly with a cap, and heated in a heat block at 100° C. for 140 minutes to decompose methanol. During heating, the sample was stirred every 30 minutes. Then, it was cooled to room temperature, and 1 mL of pure water was added and stirred vigorously. After allowing to stand, the lower layer (the chloroform layer) of the separated bilayer was aspirated with a Pasteur pipet, and filtered with a Millex-FH PVDF filter with a diameter of 0.45 µm (manufactured by Millipore). To 500 µl of the filtrated chloroform layer, 0.1 vol % of methyl caprylate which is an internal standard was added and mixed to prepare a sample. The GC instrument used was Gas Chromatograph GC14B manufactured by Shimadzu Corp. and the column used was NEUTRA-BOND-1 (an inner diameter: 30 m×0.25 mm, a film thickness: 0.4 µm) manufactured by GL Science. As the carrier gas, He and $N_2$ were used, and a hydrogen flame ionization detector was used for the detection of components.

(b) Extraction and Purification of PHA Copolymer

The dry cells that accumulated the PHA copolymer were transferred to a 100 mg capped glass bottle, 100 mL of chloroform was added thereto and stirred with a stirrer for 72 hours. The solution after stirring was filtered with a No. 1 filter paper (manufactured by Advantec), and transferred to a round bottom flask. Then the filtrate was completely evaporated in a rotary evaporator to deposit the copolymer.

Then, the deposited PHA copolymer was washed in a small amount of methanol, dissolved completely in about 20 mL of chloroform, and purified by adding dropwise 400 mL of methanol in portions under stirring. The purified copolymer was recovered with a No. 1 filter paper, and dried in a hood for 48 hours.

(c) GPC (Gel Permeation Chromatography)

The number average molecular weight (Mn) and molecular weight distribution (Mw/Mn) (Mw: weight average molecular weight) of the PHA copolymer purified from the cells were determined by GPC measurement. Since polystyrenes are used as the standard, the molecular weight determined in the present invention is a relative molecular weight expressed in terms of polystyrene. The molecular weights of five polystyrenes used are 3,790, 30,300, 219,000, 756,000 and 4,230,000.

GPC samples were prepared by dissolving the purified PHA copolymer in chloroform to about 1 mg/mL and filtering by a syringe fitted with a Millex-FH PVDF filter (manufactured by Millipore) with a pore diameter of 0.45 µm.

For GPC measurement, the LC-VP series (the system controller: SCL-10AVP, the auto injector: SIL-10A VP, the fluid feeding unit: LC-10AD VP, the column oven: CT0-10A, the detector: RID-10A) manufactured by Shimadzu Corp. was used, and the columns used were K-806M and K-802 manufactured by Shodex. For the mobile phase, chloroform was used, and the total liquid flow was set at 0.8 mL/min, the column temperature at 40° C., and the sample injection volume was 50 µl. For data analysis, the GPC for CLASS-VP (manufactured by Shimadzu Corp.) was used. By drawing a calibration line from the polystyrene standards, this was compared to the sample data to calculate the molecular weight expressed in terms of polystyrene and molecular weight distribution.

(d) Differential Scanning Calorimetry (DSC)

DSC samples were prepared by weighing out about 10 mg of the purified PHA copolymer, placing it into a 5 mL sample vial, and dissolving completely in about 1-2 mL chloroform. This was dried in a hood for about three weeks to prepare a cast film. From this cast film, about 3 mg was weighed out and placed in a special aluminum pan to prepare a DSC sample. For measurement, Pyris 1 DSC manufactured by Perkin-Elmer Inc. was used. Measurement was conducted in an atmosphere of nitrogen at 20 mL/min. As the control, an aluminum pan containing no sample was used. As the condition for measurement, heating was started at temperatures from 25° C. to 200° C. at a temperature rising rate of 20° C./min, kept the temperature of 200° C. for one minute, and then rapidly cooled to −120° C. at a rate of −500° C./min. After keeping the temperature of −120° C. for one minute, it was heated to 200° C. at a temperature rising rate of 20° C./min. For analysis, an analytical software Data Analysis manufactured by Perkin-Elmer Inc. was used. The melting point Tm and the fusion enthalpy ΔHm of the measured sample were determined from the thermogram at the initial temperature rise and the glass transition temperature Tg was determined from the thermogram at the second temperature rise.

(e) Synthesis of the 3H4MV Standard

One g of $NaBH_4$ was weighed out in a 100 mL round bottom flask, and 10 mL of methanol was added thereto. To this solution was added, 3 mL of methyl isobutyryl acetate (Tokyo Kasei)/10 mL of methanol was slowly added dropwise under stirring on ice. Stirring on ice was continued until there is no heat generation, and then stirred at room temperature for 12 hours. After the reaction was completed, unreacted $NaBH_4$ was filtered off, 40 mL of chloroform was added, and washed three times with 40 mL of saturated sodium chloride. After the chloroform layer was dried, it was concentrated in a rotary evaporator to obtain a colorless transparent liquid.

(f) Gas Chromatography/Mass Spectrometry (GC/MS)

The composition of a trace amount of 3-hydroxyalkanoic acid contained in the PHA copolymer was determined by GC/MS. For qualitative measurement, the SCAN mode was used, and for quantitative measurement the SIM (selected ion monitoring) mode was used.

<Instruments>
Gas chromatograph: GC-2010 (Shimadzu Corp.)
Gas chromatography-mass spectrometer: GCMC-QC2010 (Shimadzu Corp.)
Column: Inert Cap 1 (GL Science)
Detector: Mass spectrometer (MS)
Ionization source: Electron impact ionization (EI)
Analytical software: GC MS Solution (Shimadzu Corp.)<
<Sample Preparation>
Methyl Esterification
To a screw-cap pressure-resistant test tube, a given amount of PHA was weighed out, 2 mL of a solution of sulfuric acid in methanol and 2 mL of chloroform were added thereto, and heated at 100° C. for 140 minutes under stirring for several times. After the reaction was completed, it was cooled to room temperature, 1 mL of extra pure water was added and stirred vigorously, and after allowing to stand, the lower layer was used as the sample.
Trimethylsilylation
To 200 µl of the methyl esterified sample, 300 µl of dimethylformamide and 100 µl of bis(trimethylsilyl)trifluoroacetamide were added, and heated to 70° C. for 30 minutes under stirring for several times. After the reaction was completed, it was cooled to room temperature, 1 mL of extra pure water and 1 mL of hexane were added and stirred vigorously, and after allowing to stand, the lower layer was used as the sample.
<Measurement Condition>
For calibration of mass number in MS, perfluorotributylamine was used.
As the carrier gas, helium was used and the inlet pressure was set at 120 kPa.
Temperature Conditions of Each Instrument:
GC: Sample vaporization temperature, 280° C.; Column initial temperature, 100° C.; Column final temperature, 280° C.; Column temperature rise rate, 8° C./min; Injection mode, split;
GC-MS: Ion source temperature, 230° C.; Interface temperature, 250° C.; Solvent elution time, 1.7 minute; Detector gain, 0.8 kV.
Measurement Condition
MS SCAN: Starting time, 2 minutes; Ending time, 24 minutes; Scanning speed, 1250; Starting m/z, 45.00; Ending m/z, 600.00.
The sample injection volume was set at 1 µl.
(g) $^1$H-NMR and $^{13}$C-NMR Measurement
The PHA copolymer was dissolved in $CDCl_3$ to 3% (wt/vol) to prepare a sample for measurement. The nuclear magnetic resonance instrument was used and measurement was performed at room temperature.
(5) Measurement of Mechanical Strength of the PHA Copolymer
A PHA film was fabricated, and the Young's modulus, fracture strength and breaking elongation of the PHA film were determined by tensile testing.
<Instruments>
Tensile tester: AGS-H/EZTest (Shimadzu Corp.)
Analytical software: TRAPEZIUM 2 (Shimadzu Corp.)
<Sample Preparation>
(a) Fabrication of the Cast Film
The purified polymer was dissolved in a suitable amount of chloroform, and developed on a flat petri dish. The weight of the polymer used was calculated to a thickness of 150 µm taking into account the area of the petri dish. After development, the petri dish was capped with a perforated aluminum foil, and allowed to stand on a smooth place at room temperature until chloroform vaporized completely. After drying, the film was carefully peeled off the dish, and allowed to stand at room temperature for one week. The polymer that remained stuck to the dish was peeled by dropping extra pure water in between the dish and the polymer.
(b) Fabrication of Tensile Test Strips
The fabricated cast film was cut to a length of 20 mm and a width of 3 mm to prepare the sample. For cutting, a razor was used and pressed from above the polymer.
<Measurement Condition>
The grip distance was set at 10 mm and the tensile strength at 10 mm/min, and measurement was performed at room temperature.
<Data Analysis>
The stress and the rate of elongation when the polymer broke up were set as breaking stress and breaking elongation, respectively. The Young's modulus was set as the slope of the starting point in the stress-strain curve.
The terms "the PHA copolymer of the present invention", "PHA" or "P(3HB-co-3H4MV)" used in Examples below denote "P(3HB-co-3H4MV)" and/or "P(3HB-co-3HV-co-3H4MV)."

Working Examples 1 and 2

Production of P(3HB-co-3H4MV) Using a Polymerizing Enzyme Derived from *Pseudomonas* sp. Strain 61-3

(1) Construction of a Transformant *Ralstonia Eutropha* Strain PHB$^-$4

The competent cells of *E. coli* strain 17-1 were obtained by treating the cells in the logarithmic growth phase with a calcium chloride solution. To the cells, the DNA of plasmid pBBR1"Cl$_{Ps}$AB$_{Re}$, was added, and its introduction into the cells was promoted by heat shock of a temperature rise to 42° C.

Conjugation was conducted in order to introduce the gene into *Ralstonia eutropha* strain PHB$^-$4. *E. coli* strain 17-1 having plasmid pBBR1"Cl$_{Ps}$AB$_{Re}$ introduced therein was inoculated to 1.7 mL of the LB medium, and cultured under shaking at 37° C. for 15 hours. Also, the host (*Ralstonia eutropha* strain PHB$^-$4) to which the gene is to be introduced was inoculated to 1.7 mL of the NR medium, and cultured at 30° C. for 15 hours. After culturing was completed, each of the total amount of the culture liquid was transferred to an autoclaved Eppendorf tube, and centrifuged at 12,000 rpm for 2 minutes. To an *E. coli* strain 17-1 containing an antibiotic, 500 µl of the LB medium was added and further centrifuged to remove the antibiotic completely. After discarding part of the supernatant so as to leave about 50 µl thereof, the *E. coli* strain 17-1 and the *Ralstonia eutropha* strain PHB$^-$4 were mixed, added dropwise to the LB agar medium, and, after drying, cultured at 30° C. for 5 hours. Subsequently, it was streaked on the Simmons citrate medium containing an antibiotic, and cultured at 30° C. for 2 days. A single colony thus obtained was streaked again on the Simmons citrate medium and cultured at 30° C. for 2 days. A single colony (transformant *Ralstonia eutropha* strain) thus isolated was used in the following experiments.

(2) Culturing of the Transformant *Ralstonia eutropha* Strain

For culturing of the transformant *Ralstonia eutropha* strain, the MS medium was used. One platinum loopful of a single colony isolated on the Simmons citrate medium was inoculated on 1.7 mL of the NR medium, and cultured under shaking at 30° C. for 12 hours (preculture). One mL of this culture liquid was inoculated on 100 mL of the MS medium containing 20 g/L of fructose, an antibiotic and 4-methylvaleric acid or 4-methylpentene acid (both, 1 g/L), and cultured under shaking at 30° C. and 130/min for 72 hours (main culture). For comparison, a similar culturing was conducted by adding L-valine or L-leucine.

After culturing was completed, the culture liquid was transferred to a 250 mL centrifuge tube and centrifuged at 4° C., 6,000 rpm (4,050×g) for 10 minutes to collect the cells. After centrifuging the cells, they were suspended in about 20 mL of water, and centrifuged again at 4° C., 6,000 rpm for 10 minutes to collect the cells, and the supernatant was removed. The pellet of the collected cells was suspended in 2-3 mL of extra pure water, transferred to a 5 mL polypropylene vessel, a holed parafilm was attached thereto, lyophilized at −80° C., and dried under vacuum for 72 hours to obtain the dry cells.

Figure 2:
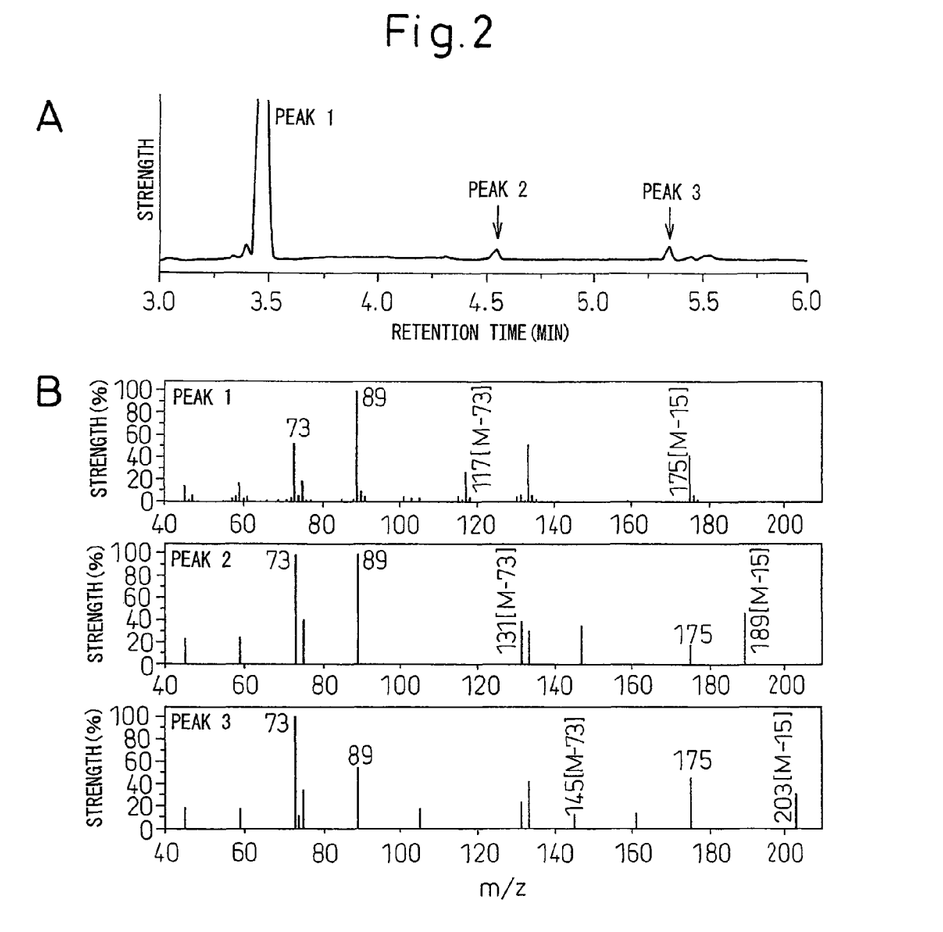
FIG. 2 is a drawing that shows the result of GC-MS analysis of a silylated 3HA methyl ester. (A) A total ion chromatogram; (B) The ion fragment patterns of peak 1 (3.5 minutes), peak 2 (4.6 minutes) and peak 3 (5.3 minutes) correspond to a silylated 3HB, a silylated 3HV and a silylated 3H4WV, respectively.
Figure 3:
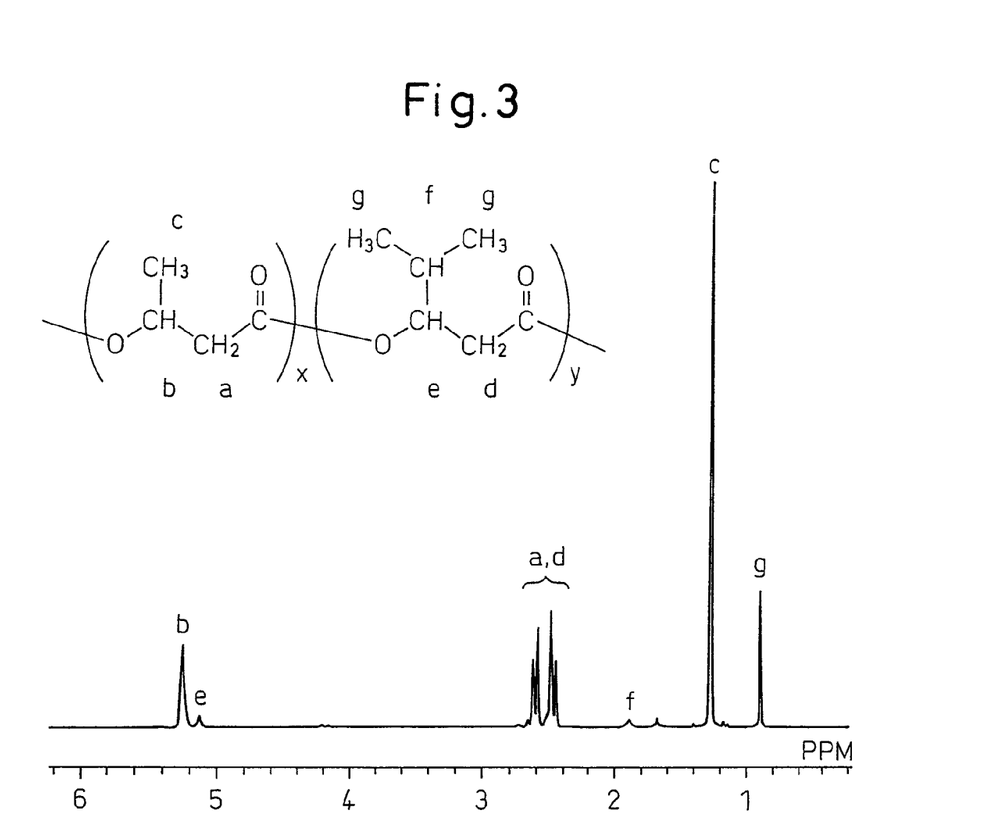
FIG. 3 is a drawing that shows the 500 MHz $^1$H-NMR spectrum of P(3HB-co-3H4MV) isolated from *R. eutropha* (PhaCl$_{Ps}$) cultured on fructose (20 g/l) and 4-methyl valeric acid (4MV) (1 g/l). In the chemical formula of P(3HB-co-3H4MV), x and y represent the numbers of repeats.
Figure 4:
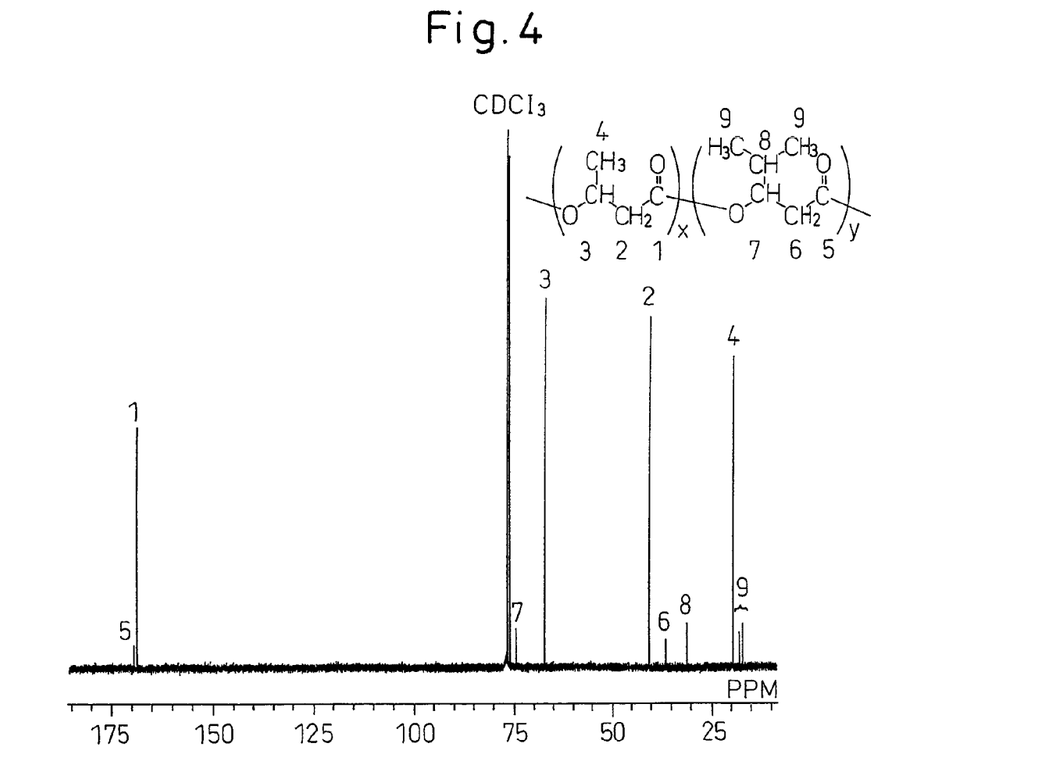
FIG. 4 is a drawing that shows the 125 MHz $^{13}$C-NMR spectrum of P(3HB-co-3H4MV) isolated from *R. eutropha* (phaCl$_{Ps}$) cultured on fructose (20 g/l) and 4-methyl valeric acid (4MV) (1 g/l).

By purifying the dry cells as described above, PHA was obtained, and its structure was analyzed by GC-MS (FIGS. 1 and 2), $^1$H-NMR (FIG. 3) and $^{13}$C-NMR (FIG. 4). Table 1 shows the molecular weight and GC retention time of each 3HA methylester.

TABLE 1

Molecular weight and gas chromatography (GC) of 3HA methylesters Retention time

| 3HA[a] units | Molecular weight | GC retention time (min)[b] |
|---|---|---|
| 3HA methylester | 118 | 2.2 |
| 3HV methylester | 132 | 2.8 |
| 3H4MV methylester | 146 | 3.5 |
| 3HHx methylester | 146 | 3.8 |
| Silylated 3HA methylester | 190 | 3.5 |
| Silylated 3HV methylester | 204 | 4.5 |
| Silylated 3H4MV methylester | 218 | 5.3 |
| Silylated 3HHx methylester | 218 | 5.7 |

[a]3HB: (R)-3-hydroxybutanoic acid; 3HV: (R)-3-hydroxyvaleric acid; 3H4MV: (R)-3-hydroxy-4-methyl valeric acid; 3HHx: (R)-3-hydroxyhexanoic acid
[b]The temperature program of GC started with 100° C. for one minute, followed by a temperature rise to 280° C. in successive steps of 8° C./minute.

From FIG. 1, it was found for the first time that, even in the absence of a precursor, P(3HB-co-3H4MV) having 3H4MV as the building block can be obtained ((a) in FIG. 1). $^1$H-NMR data and $^{13}$C-NMR data of P(3HB-co-3H4MV) are shown below.

$^1$H-NMR (500 MHz, CDCl$_3$) δ (ppm): 5.30-5.23 (m, CC$\overline{\text{HCH}_3}$ of 3HB), 5.13 (d, CC$\overline{\text{HCH}_2}$ of 3H4MV), 2.67-2.44 (m, $\overline{\text{CCH}_2}$CO of 3HB), 1.89 (dd, $\overline{\text{CCH}_2}$CO of 3H4MV), 1.27 (dd, CC$\overline{\text{H}_3}$ of 3HB), 0.90 (d, C(C$\overline{\text{H}_3}$)$_2$ of 3H4MV). $^{13}$C-NMR (125 MHz, CDCl$_3$) δ (ppm): 169.1 (the carbonyl carbon of the 3HB unit), 169.7 (the carbonyl carbon of the 3H4MV unit).

It was also found that, in the presence of a precursor, P(3HB-co-3H4MV) having a high composition ratio of 3H4MV can be obtained ((b) in FIG. 1). The results are summarized in Table 2. On the other hand, when L-leucine or L-valine was added in stead of the precursor, no P(3HB-co-3H4MV) was detected.

TABLE 2

The composition of PHA synthesized from fructose and a 3H4MV analog by *Ralstonia eutropha* strain PHB$^-$4 (phaCI$_{Ps}$)[a]

| | Substrate | | Dry cell mass (g/L) | PHA content (wt %) | PHA composition (mol %) | | |
|---|---|---|---|---|---|---|---|
| | Carbon source | Precursor | | | 3HB | 3HV | 3H4MV |
| Work. Ex. 1 | Fructose | 4-Methyl-2-pentene acid | 0.9 | 26 ± 3 | 89.5 | 1.2 | 9.3 |
| Work. Ex. 2 | Fructose | 4-methylvaleric acid (4MV) | 1.5 | 46 ± 2 | 86.2 | 0.9 | 12.9 |
| Comp. Ex. 1 | Fructose | None | 1.7 | 49 ± 2 | 98.9 | 0.5 | 0.6 |
| Comp. Ex. 2 | Fructose | Leucine | 3.1 | 44 ± 4 | 99.6 | 0.4 | 0 |
| Comp. Ex. 3 | Fructose | Valine | 3.1 | 59 ± 5 | 99.5 | 0.5 | 0 |

[a]The results are the mean and standard deviation from three independent cultures.
[b]The 3H4MV analog was added to the MS medium containing fructose (20 g/L) to a final concentration of 1.0 g/L.

Working Examples 3 to 6

Production of P(3HB-co-3H4MV) from Fructose and 4-Methylvaleric Acid by a *Ralstonia eutropha* Strain Having an *Aeromonas caviae*-Derived Polymerizing Enzyme Introduced Therein In a manner similar to Working Example 2 except that plasmid pBBREE32d13 was used in stead of plasmid pBBR1"Cl$_{Ps}$AB$_{Re}$, it was investigated whether the gene of polyhydroxyalkanoic acid-polymerizing enzyme derived from *Aeromonas caviae* can incorporate 3H4MV. Also, a mutant (NSDG mutant) in which asparagine at position 149 of the polyhydroxyalkanoic acid-polymerizing enzyme derived from *Aeromonas caviae* was replaced with serine and aspartic acid at position 171 was replaced with glycine, was prepared according to the method described in FEMS Microbiol Lett, 277 (2007), pp. 217-222 in order to investigate whether the gene of the polymerizing enzyme encoding said mutant can incorporate 3H4MV. The results are shown in Table 3.

TABLE 3

The biosynthesis of PHA from fructose and 4-methylvaleric acid by a *Ralstonia eutropha* strain[a]

| | Microbial strain | Dry cell mass (g/L) | PHA content (wt %) | PHA composition (mol %) 3HB | 3HV | 3H4MV | Molecular weight Mn (×10³) | Mw/Mn |
|---|---|---|---|---|---|---|---|---|
| Work. Ex. 3 | *R. eutropha* H16 (wild type) | 3.1 | 69 ± 1 | 98.6 | 0.7 | 0.7 | 320 | 2.5 |
| Work. Ex. 4 | PHB⁻4 having phaCl$_{Ps}$[b] | 1.5 | 46 ± 2 | 86.2 | 0.9 | 12.9 | 52 | 1.4 |
| Work. Ex. 5 | PHB⁻4 having phaCl$_{Ac}$[c] | 2.2 | 65 ± 3 | 94.0 | 0.5 | 5.5 | 330 | 2.2 |
| Work. Ex. 6 | PHB⁻4 having phaCl$_{Ac}$(NSDG mutant)[d] | 2.9 | 66 ± 3 | 89.6 | 0.4 | 10.0 | 400 | 4.1 |

[a] The results of dry cell mass, PHA content and PHA composition are the means and standard deviations from three independent cultures. The cells were cultured in a MS medium containing fructose (20 g/L) and 4-methylvaleric acid.
[b] The PHA synthetase gene derived from *Pseudomonas* sp. strain 61-3
[c] The PHA synthetase gene derived from an *Aeromonas caviae* strain
[d] The PHA synthetase gene mutant derived from *Aeromonas caviae* (N149→S and D171→G)

From FIG. 3, it was found that though the PHA synthetase gene derived from the wild type *Raistonia eutropha* strain H16 incorporated 3H4MV, the incorporation rate was higher for the PHA synthetase gene derived from *Pseudomonas* sp. strain 61-3, the PHA synthetase gene derived from an *Aeromonas caviae* strain and the PHA synthetase mutant gene derived from an *Aeromonas caviae* strain.

Working Example 7

Effect of 4-Methylvaleric Acid Concentration

P(3HB-co-3H4MV) was produced in a manner similar to Working Examples 4 and 6 except that the concentration of 4-methylvaleric acid was varied. The results are shown in Table 4.

TABLE 4

The production of P(3HB-co-3H4MV) from fructose and 4-methyl valeric acid (4MV) by various *Ralstonia eutropha* strains[a]

| Microbial strain | 4MV (g/L) | Dry cell mass (g/L) | PHA content (wt %) | PHA composition (mol %) 3HB | 3HV | 3H4MV | Sample No. |
|---|---|---|---|---|---|---|---|
| PHB⁻4 having phaCl$_{Ps}$ | 0 | 1.9 | 56 ± 1 | 98.9 | 0.5 | 0.6 | (1) |
| | 0.25 | 2.0 | 64 ± 2 | 99.0 | 0.1 | 0.9 | (2) |
| | 0.5 | 2.0 | 62 ± 3 | 95.1 | 0.4 | 4.5 | (3) |
| | 0.75 | 1.9 | 62 ± 2 | 90.4 | 0.6 | 9.0 | (4) |
| | 1 | 1.5 | 46 ± 2 | 86.2 | 0.9 | 12.9 | (5) |
| | 1.25 | 1.5 | 48 ± 1 | 84.2 | 1.3 | 14.5 | (6) |
| | 1.5 | 1.3 | 38 ± 5 | 82.2 | 1.6 | 16.2 | (7) |
| | 2 | 0.7 | 1.4 ± 1 | —[b] | —[b] | —[b] | (8) |
| PHB⁻4 having the NSDG mutant gene | 0 | 3.9 | 73 ± 1 | 100.0 | 0 | 0 | (9) |
| | 0.25 | 3.6 | 72 ± 1 | 98.2 | 0 | 1.8 | (10) |
| | 0.5 | 3.3 | 71 ± 2 | 95.6 | 0 | 4.4 | (11) |
| | 0.75 | 3.1 | 71 ± 3 | 92.7 | 0.3 | 7.1 | (12) |
| | 1 | 2.9 | 66 ± 3 | 89.6 | 0.4 | 10.0 | (13) |
| | 1.25 | 2.4 | 65 ± 3 | 84.9 | 0.5 | 14.6 | (14) |
| | 1.5 | 2.3 | 63 ± 2 | 82.0 | 0.5 | 17.5 | (15) |
| | 2 | 1.7 | 53 ± 1 | 73.8 | 0.7 | 25.6 | (16) |
| | 2.5 | 1.5 | 56 ± 6 | 67.7 | 0.9 | 31.4 | (17) |
| | 3 | 1.2 | 35 ± 8 | 60.4 | 0.7 | 38.9 | (18) |

[a] The results of dry cell mass, PHA content and PHA composition are the means and standard deviations from three independent cultures. The cells were cultured in a MS medium containing fructose (20 g/L) and different concentrations of 4-MV.
[b] The amount was too small to be determined.

Working Example 8

Molecular Weight of P(3HB-co-3H4MV), and the Thermal and Mechanical Characteristics of Solution-Cast Films Containing P(3HB-co-3H4MV)

Solution-cast films containing copolymers of sample Nos. (1) to (18) prepared in Working Example 7 were prepared as described above (the sample Nos. of the films obtained are (1') to (18')), and the thermal and mechanical characteristics thereof were determined (Table 5).

Working Example 9

Changes with Time in Mechanical Characteristics of (3HB-co-3H4MV)

Figure 6:
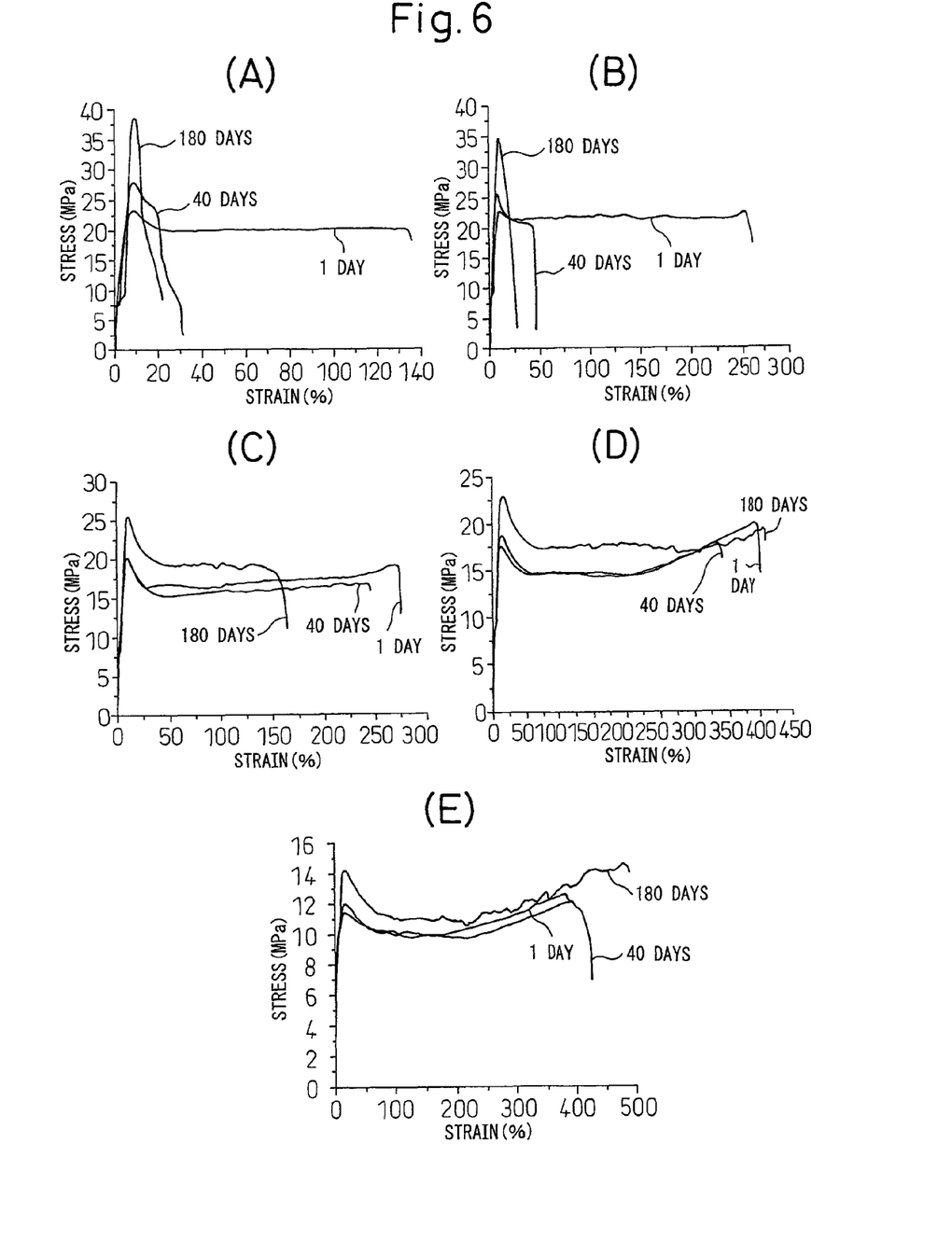
FIG. 6 shows the stress-strain curve of each film, stored for one day, 40 days and 180 days, of (A) P(3HB-co-7 mol % 3H4MV); (B) P(3HB-co-9 mol % 3H4MV); (C) P(3HB-co-14 mol % 3H4MV); (D) P(3HB-co-16 mol % 3H4MV); and (E) P(3HB-co-22 mol % 3H4MV) produced from *R. eutropha* (phaC$_{AC}$ (NSDG mutant)).

Samples (1') to (18') obtained in Working Example 8 were stored at room temperature for one day, 40 days, and 180 days, and then tensile strength and breaking elongation were determined (Table 6, FIG. 6).

TABLE 5

Molecular weight of P(3HB-co-3H4MV) synthesized by a recombinant *Ralstonia eutropha* strain, and thermal and mechanical characteristics of P(3HB-co-3H4MV) solution-cast films

| Microbial strain | Sample No. | 3H4MV fraction (mol %) | Thermal characteristics Tm (° C.) | Tg (° C.) | ΔHm (J/g) | Mechanical characteristics Tensile strength (MPa) | Young's modulus (MPa) | Breaking elongation (%) | Molecular weight Mn (×10$^4$) | Mw (×10$^4$) | Mw/Mn |
|---|---|---|---|---|---|---|---|---|---|---|---|
| PHB$^-$4 having phaC1$_{Ps}$ | (1') | 0 | 157, 171 | 0 | 74 | 28.9 | 1736 | 6 | 23 | 31 | 1.3 |
| | (2') | 1 | 153, 167 | −1 | 77 | 13.8 | 762 | 8 | 19 | 34 | 1.8 |
| | (3') | 4 | 152, 168 | −2 | 69 | 16.8 | 935 | 9 | 20 | 31 | 1.6 |
| | (4') | 7 | 149, 165 | −2 | 39 | 15.6 | 861 | 7 | 14 | 25 | 1.8 |
| | (5') | 13 | 126, 138 | −3 | 23 | 17.4 | 655 | 23 | 10 | 14 | 1.4 |
| | (6') | 14 | 125, 137 | −3 | 21 | 17.3 | 590 | 23 | 10 | 15 | 1.5 |
| | (7') | 15 | 120, 135 | −4 | 13 | 16.1 | 531 | 24 | 9 | 13 | 1.4 |
| PHB$^-$4 having the NSDG mutant gene | (9') | 0 | 159, 172 | 0 | 53 | 29.3 | 1340 | 6 | 158 | 468 | 2.9 |
| | (10') | 2 | 157, 169 | −1 | 47 | 29.5 | 1688 | 10 | 69 | 310 | 4.5 |
| | (11') | 4 | 154, 166 | −1 | 34 | 33.4 | 1351 | 13 | 50 | 234 | 4.7 |
| | (12') | 7 | 149, 162 | −2 | 37 | 23.5 | 874 | 32 | 46 | 184 | 4.0 |
| | (13') | 9 | 146, 159 | −2 | 33 | 20.8 | 566 | 46 | 40 | 163 | 4.1 |
| | (14') | 14 | 136, 148 | −2 | 27 | 16.6 | 509 | 246 | 45 | 147 | 3.3 |
| | (15') | 16 | 133, 143 | −2 | 11 | 17.7 | 382 | 341 | 39 | 131 | 3.4 |
| | (16') | 22 | 126 | −2 | 8 | 12.1 | 241 | 425 | 43 | 134 | 3.1 |
| | (17') | 30 | 118 | −4 | 2.6 | ND[b] | ND[b] | ND[b] | 47 | 125 | 2.7 |
| | (18') | 38 | 113 | −4 | 0.7 | ND[b] | ND[b] | ND[b] | 43 | 105 | 2.5 |

[a] The PHA composition of the purified copolymer samples was determined by GC. Mn: number average molecular weight; Mw: weight average molecular weight; Mw/Mn: multiple degrees of dispersion; Tg: glass transition point; Tm: melting point; ΔHm: crystal-melting enthalpy. The Copolymer P(3HB-co-3H4MV) samples were obtained from PHB$^-$4 having phaC1$_{Ps}$ and PHB$^-$4 having the NSDG mutant gene.
[b] ND: Not detected.

The higher the crystal-melting enthalpy (ΔHm) is, the higher the crystallinity of the PHA copolymer obtained becomes. When crystallinity becomes higher, the hardness of said PHA copolymer increases but it becomes brittle.

Figure 5:
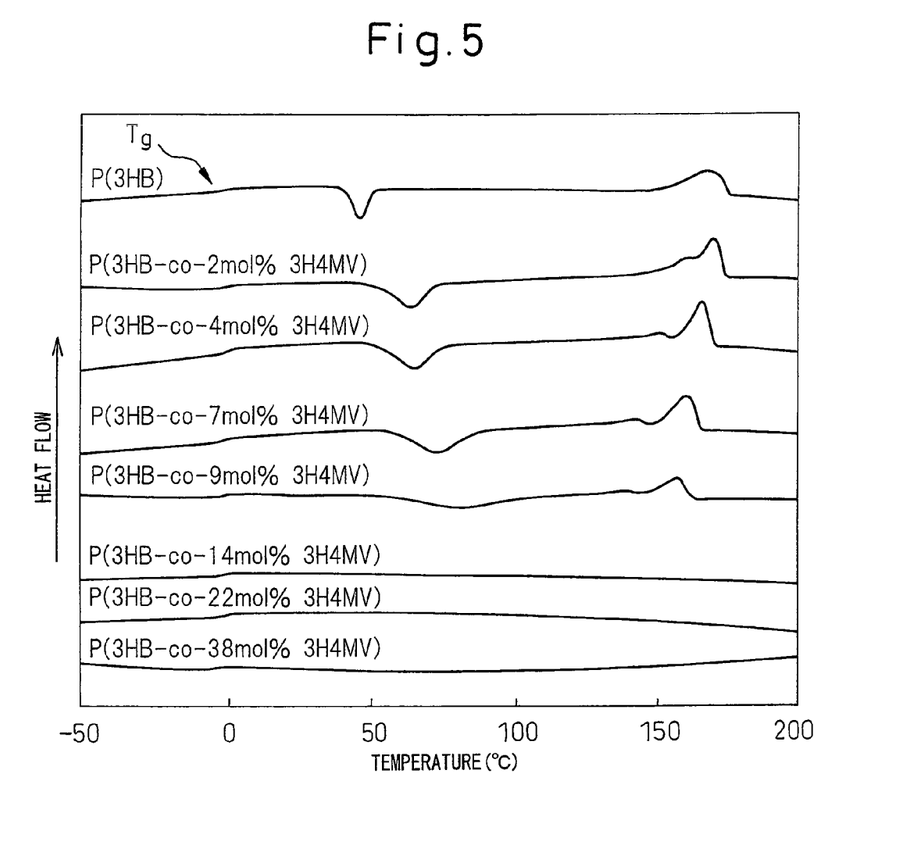
FIG. 5 is a drawing that shows changes in the DSC heat capacity of solution-cast films of various P(3HB-co-3H4MV) samples isolated from *R. eutropha* (phaC$_{AC}$ (NSDG mutant)). The heating temperature is 20° C./minute.
Figure 7:
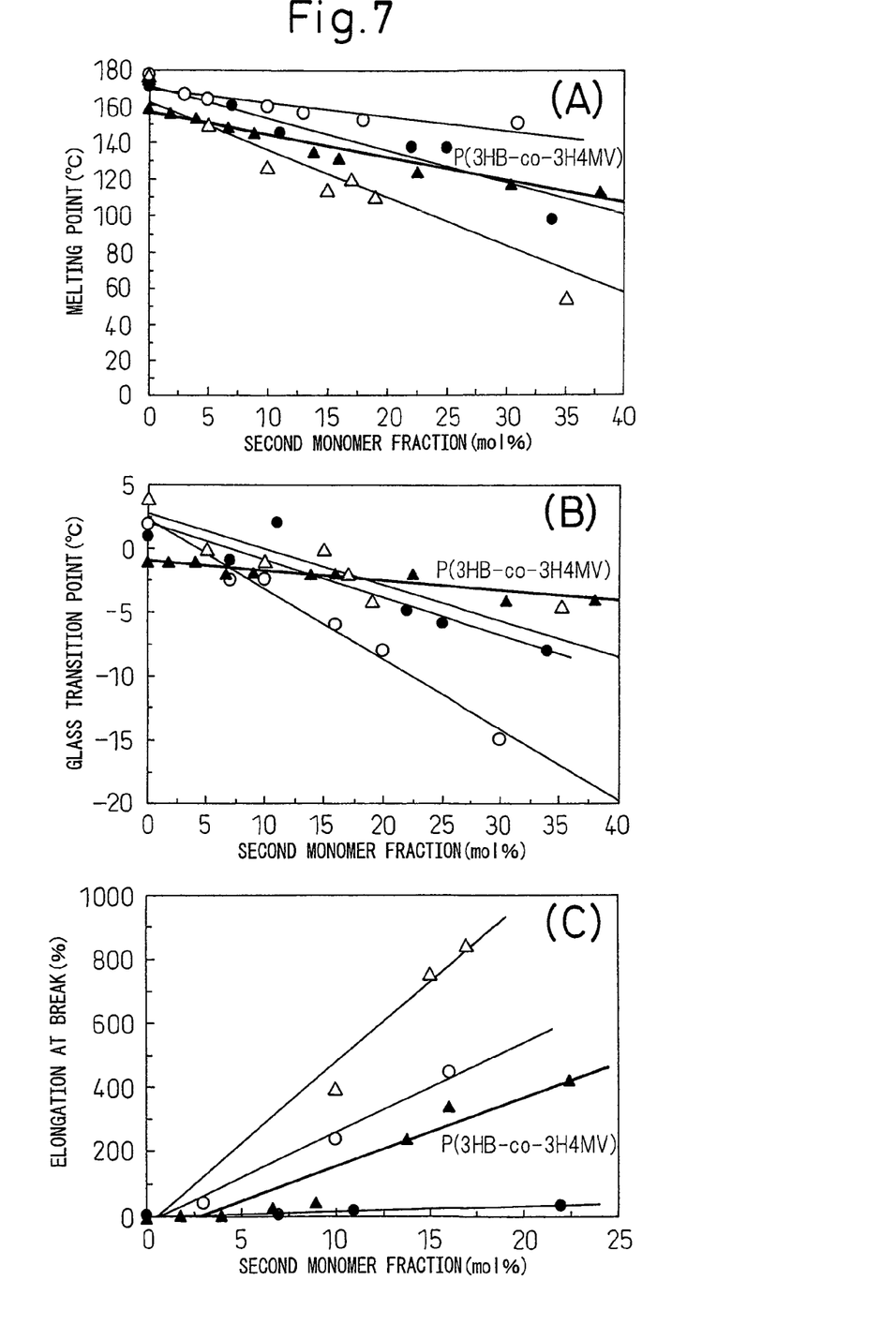
FIG. 7 is a drawing that shows (A) the relation of melting point (Tm) and the content of the second monomer units; (B) the relation of glass transition temperature (Tg) and the content of the second monomer units; and (C) the relation of the ratio (%) of breaking elongation and the content of the second monomer units, regarding the following copolymer: P(3HB-co-3H4MV) fraction (black triangle), P(3HB-co-3HHx) fraction (white triangle), P(3HB-co-3HV) fraction (black circle), and P(3HB-co-4HB) fraction (white circle). The second monomer fraction on the abscissa represents the content (mol %) of 3H4MV units. The trend line of P(3HB-co-3H4MV) is shown in a thick line.

In accordance with the present invention, specifically in samples (6), (7) and (14) to (18) containing 14 mol % or more of 3H4MV, the crystallinity of the PHA copolymer is low, and samples (6'), (7') and (14') to (16') among them were actually found to have a high flexibility from the values of the Young's modulus and breaking elongation. Changes in DSC heat capacity for samples (9') to (16') and (18') are shown in FIG. 5. Also, for P(3HB-co-3H4MV), P(3HB-co-3HHx), P(3HB-co-3HV) and P(3HB-co-4HB), (A) relation between the melting point (Tm) and the content of the second monomer units; (B) relation between the glass transition point (Tg) and the content of the second monomer units; and (C) relation between the rate (%) of breaking elongation and the content of the second monomer units, are shown in FIG. 7.

For reference, the melting point of P(3HB-co-3HV) in which the 3HV composition is 14 mol % is 150° C. (P. Holms, in Development in Crystalline Polymers-2, D. C. Bassett, Ed., Elsevier, London, 1988, pp. 1-65), the melting point of P(3HB-co-3HHx) in which the 3HHx composition is 15 mol % is 115° C. (Micromolecules, 1995, Vol. 28, pp. 4822-4828), and the melting point of the 3HB homopolymer is 174° C.

TABLE 6

Mechanical characteristics of P(3HB-co-3H4MV) solution-cast films stored for one day, 40 days, and 180 days

| Sample No. | 3H4MV fraction (mol %) | Elapsed time (days) | Tensile strength (MPa) | Breaking elongation (%) |
|---|---|---|---|---|
| (12') | 7 | 1 | 19.7 | 136 |
| | | 40 | 23.5 | 32 |
| | | 180 | 21.8 | 22 |
| (13') | 9 | 1 | 22.3 | 263 |
| | | 40 | 20.8 | 46 |
| | | 180 | 23.3 | 27 |
| (14') | 14 | 1 | 18.6 | 275 |
| | | 40 | 16.6 | 245 |
| | | 180 | 18.2 | 164 |
| (15') | 16 | 1 | 19.5 | 400 |
| | | 40 | 17.7 | 341 |
| | | 180 | 18.9 | 409 |
| (16') | 22 | 1 | 12.3 | 390 |
| | | 40 | 12.1 | 425 |
| | | 180 | 14.3 | 489 |

From Table 6 and FIG. 6, it was found that the solution-cast films containing the PHA copolymer of the present invention retain the mechanical characteristics at the time of production even after storing for 180 days, and thus are highly stable.

The invention claimed is:

1. A method of producing a polyhydroxyalkanoic acid copolymer comprising: culturing, in the presence of a carbon source and a precursor of (R)-3-hydroxy-4-methyl valeric acid, a transformed microorganism in which the gene of polyhydroxyalkanoic acid-polymerizing enzyme has been introduced; wherein the microorganism is selected from the group consisting of *Escherichia coli*, *Ralstonia* sp., and *Pseudomonas* sp, and isolating the polyhydroxyalkanoic acid copolymer comprising at least (R)-3-hydroxy-4-methyl valeric acid units from the culture.

2. The method according to claim 1, wherein the precursor is selected from the group consisting of 4-methyl valeric acid, 4-methyl pentene acid, and a mixture thereof.

3. The method according to claim 1, wherein the precursor is added at a concentration of 0.1-5.0 g/L.

4. The method according to claim 1 wherein the gene of polyhydroxyalkanoic acid-polymerizing enzyme is obtained from a microorganism selected from the group consisting of *Pseudomonas* sp, strain 61-3, *Pseudomonas stutzeri* A33, *Allochromatium vinosum*, *Bacillus megaterium*, *Bacillus cereus*, *Bacillus* sp. INT005, *Lamprocystis roseopersicina*, *Norcardia corallina*, *Rhodobacter shaeroides*, *Ralstonnia eutropha*, *Rhodococcus* sp. NCIMB 40126, *Thiocapsa pfennigii*, *Aeromonas caviae*, and *Aeromonas hydrophila*.

5. The method according to claim 1 wherein the gene of polyhydroxyalkanoic acid-polymerizing enzyme is obtained from *Pseudomonas* sp, strain 61-3 or *Aeromonas caviae*.

6. The method according to claim 1 wherein the gene of polyhydroxyalkanoic acid-polymerizing enzyme is obtained from *Aeromonas caviae*.

7. The method according to claim 1, wherein the carbon source is a monosaccharide.

8. The method according to claim 7, wherein the carbon source is fructose.

9. The method according to claim 1, wherein the polyhydroxyalkanoic acid copolymer comprises the (R)-3-hydroxy-4-methyl valeric acid units and (R)-3-hydroxybutanoic acid units.

10. The method according to claim 1, wherein the polyhydroxyalkanoic acid copolymer comprises the (R)-3-hydroxy-4-methyl valeric acid units, (R)-3-hydroxybutanoic acid units, (R)-3-hydroxyvaleric acid units, and optionally (R)-3-hydroxyhexanoic acid units.

11. The method according to claim 1, wherein the polyhydroxyalkanoic acid copolymer comprises 14 mol % or more of the (R)-3-hydroxy-4-methyl valeric acid units.

12. The method according to claim 11, wherein the polyhydroxyalkanoic acid copolymer comprises 14 mol % to 40 mol % of the (R)-3-hydroxy-4-methyl valeric acid units.

* * * * *